US00PP32663P2

(12) United States Plant Patent
Sproul

(10) Patent No.: US PP32,663 P2
(45) Date of Patent: Dec. 22, 2020

(54) FLORIBUNDA ROSE PLANT NAMED 'SPROGREATPINK'

(50) Latin Name: *Rosa hybrida*
Varietal Denomination: Sprogreatpink

(71) Applicant: The Conard-Pyle Company, West Grove, PA (US)

(72) Inventor: James Sproul, Bakersfield, CA (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 16/602,929

(22) Filed: Dec. 30, 2019

(51) Int. Cl.
*A01H 5/02* (2018.01)
*A01H 6/74* (2018.01)

(52) U.S. Cl.
USPC ..... Plt./148
CPC ..... *A01H 6/749* (2018.05)

(58) Field of Classification Search
USPC ..... Plt./148
CPC ..... A01H 6/749; A01H 5/02
See application file for complete search history.

(56) References Cited

U.S. PATENT DOCUMENTS

PP16,202 P2 1/2006 Radler
PP23,549 P3 4/2013 Sproul

*Primary Examiner* — Keith O. Robinson
(74) *Attorney, Agent, or Firm* — Panitch Schwarze Belisario & Nadel LLP

(57) ABSTRACT

A new and distinct variety of floribunda rose plant, herein referred to by its cultivar name, 'Sprogreatpink', is provided which forms abundantly on a substantially continuous basis attractive, cup-like shaped deep pink colored blossoms. Attractive, glossy, dark green foliage is formed, which contrasts beautifully with the blossoms. The growth habit is very bushy and compact. The new variety is well suited for providing attractive ornamentation in the landscape.

1 Drawing Sheet

Botanical/commercial classification: Latin name: *Rosa hybrida.*

Varietal denomination: 'Sprogreatpink'.

SUMMARY OF THE INVENTION

The new variety of *Rosa hybrida* floribunda rose plant was created during April of 2011 in Bakersfield, Calif., U.S.A., by artificial pollination wherein two parents were crossed which previously had been studied in the hope that they would contribute the desired characteristics. The female parent (i.e., the seed parent) was the progeny of an unnamed seedling (non-patented) and the 'Sprothrive' variety (U.S. Plant Pat. No. 23,549). The male parent (i.e., the pollen parent) was the 'Radtko' variety (U.S. Plant Pat. No. 16,202).

The parentage of the new variety can be summarized as follows:

(unnamed seedling x 'Sprothrive') x 'Radtko'

The seeds resulting from the above pollination were sown and small plants were obtained which were physically and biologically different from each other. Selective study resulted in the identification of a single plant of the new variety.

It was found that the new variety of Floribunda rose plant of the present invention possesses the following combination of characteristics:

(a) forms attractive, cup-like shaped, deep pink colored blossoms abundantly and substantially continuously,
(b) displays a very bushy and compact growth habit,
(c) forms vigorous vegetation, and (d) provides attractive ornamental glossy, dark green foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the female parent, the (unnamed breeder seedling x 'Sprothrive') variety (i.e., the seed parent) displays less petals and has less warmth in the pink flower color compared to the new variety. In addition, the 'Radtko' variety (i.e., the pollen parent) provides less glossy foliage, larger blooms, and less blooms per plant compared to the new variety. Moreover, the new variety can be readily distinguished from other similar non-parental varieties. For example, the 'Jacpoulp' variety (not patented in the U.S.) displays lighter pink colored blossoms compared to the new variety.

The new variety has been found to undergo asexual propagation at Wasco, Calif. and at Cochranville, Pa. by a number of routes, including vegetative cuttings. Asexual propagation by vegetative cuttings at Wasco, Calif. and at Cochranville, Pa. has shown that the characteristics of the new variety are stable and are strictly transmissible by such asexual propagation from one generation to another. Accordingly, the new variety undergoes asexual propagation in a true-to-type manner.

The new variety has been named 'Sprogreatpink'.

The first offer for sale was on Jan. 9, 2019 in Baltimore, Md.

BRIEF DESCRIPTION OF THE PHOTOGRAPH

The accompanying photograph of FIG. 1 shows as nearly true as it is reasonably possible to make the same, in a color illustration of this character, a typical specimen of the new variety. The rose plant of the new variety was approximately three years of age and was observed during May 2019 while growing on its own roots and growing outdoors at Cochranville, Pa., U.S.A.

FIG. 1—illustrates a specimen a plant with open blossoms.

DETAILED BOTANICAL DESCRIPTION

The chart used in the identification of the colors is that of The Royal Horticultural Society (R.H.S. Colour Chart, 2015 edition), London, England. The terminology which precedes reference to the chart has been added to indicate the corresponding color in more common terms. The description is based on the observation of three-year-old specimens of the new variety during May while growing on their own roots in a three-gallon container at Cochranville, Pa., U.S.A.

Commercial classification: Floribunda Rose Plant.

Plant:

*Habit*.—Very bushy and compact.

*Height*.—Approximately 40.0 cm on average from the top of the soil plane.

*Width*.—Approximately 40.0 cm on average.

Branches:

*Color*.—Young stems: commonly near Yellow-Green Group 144A. — old wood: commonly near Yellow-Green Group 146B.

*Length*.—Main stems: approximately 40.0 cm on average. — secondary stems: approximately 16.0 cm on average.

*Diameter*.—Main stems: approximately 5.0 mm on average. — secondary stems: approximately 3.0 mm on average.

*Thorns*.—Young thorns: length is approximately 6.0 mm on average, width is approximately 3.0 mm on average at point of attachment, and color is commonly near Greyed-Red Group 180A. — old thorns: length is approximately 7.0 mm on average, width is approximately 4.0 mm on average at point of attachment, and color is commonly near Brown Group N200B.

Foliage:

*General appearance*.—Dark green with a glossy aspect.

*Number of leaflets*.—3, 5, and 7.

5-*leaflet leaf*.—Length: approximately 9.0 cm on average. — width: approximately 5.0 cm on average.

*Young foliage*.—Upper surface color: commonly near Yellow-Green Group 144A with indistinguishable venation except the midvein, which is commonly near Greyed-Red Group 178A. — under surface color: commonly near Yellow-Green Group 144B with indistinguishable venation.

*Old foliage*.—Upper surface color: commonly near Green Group 137A with venation commonly near Green Group 137B. — under surface color: commonly near Green Group 137C with venation commonly near Green Group 137D.

Leaflets:

*Shape*.—Ovate; apex is rounded; and base is rounded.

*Texture*.—Upper and under surface is smooth.

*Terminal leaflet*.—Length: approximately 3.0 cm on average. — width: approximately 2.7 cm on average.

*Lower leaflet*.—Length: approximately 2.5 cm on average. — width: approximately 2.0 cm on average.

*Leaf margin*.—Serrate.

*Leaf undulation*.—Moderate.

*Petiole*.—Upper surface: color is commonly near Greyed-Red Group 178A and texture is smooth. — under surface: color is commonly near Green Group 138B and texture is glandular with some small prickles. — length: approximately 3.0 cm on average. — diameter: approximately 1.5 mm on average.

*Rachis*.—Color of upper surface: commonly near Greyed-Orange Group 176A. — color of under surface: commonly near Green Group 138B. — length: approximately 6.0 cm on average. — diameter: approximately 1.5 mm on average.

*Stipules*.—Margin: entire to erose. — length: approximately 1.2 cm on average. — width: approximately 4.0 mm on average. — color of upper surface: commonly near Green Group 143B with some mixing of near Greyed-Orange Group 176A particularly close to the innermost portion. — color of lower surface: commonly near Greyed-Orange Group 176A.

Inflorescence:

*Number of flowers*.—Generally about 7 blooms open on average on a plant at once.

*Number of blooms per stem*.—Generally 1 bloom per stem on average.

*Bud*.—Shape: ovoid. — length: approximately 1.5 cm on average. — width: approximately 1.3 cm on average. — color when opening: commonly near Red Group 53B.

*Sepals*.—Number: commonly 5. — length: approximately 2.0 cm on average. — width: approximately near 9.0 mm on average. — margin: entire with extensions on two or three sepals measuring approximately 5.0 mm in length on average and 1.0 mm in width on average. — upper surface color and texture: commonly near Yellow-Green Group 144A; covered in short pubescence. — under surface color and texture: commonly near Yellow-Green Group 144B; puberulent.

*Receptacle*.—Achenes stand on the bottom and wall. — color: commonly near Yellow-Green Group 144A. — diameter: approximately 1.0 cm on average. — depth: approximately 1.0 cm on average. — surface texture: smooth. — shape: round.

*Peduncle*.—Length: approximately 3.5 cm on average. — diameter: approximately 2.0 mm on average. — surface texture: sparely covered in short, flexible thorns that measure less than 1.0 mm in length. — color: commonly near Yellow-Green Group 144A.

*Flower*.—Diameter: approximately 8.0 cm on average. — height: approximately 5.0 cm on average. — duration: flower is on the plant approximately 10 days. — shape: cuplike. — form: double. — profile: flat to slightly concave. — number of petals under normal conditions: approximately 15 petals on average. — shape of the petal: overall: broadly obovate. apex: rounded to obcordate. base: cuneate. — petal length: approximately 4.0 cm on average. — petal width: approximately 3.8 cm on average. — petal margin: entire with a moderate undulation. — petal drop: good. — petaloids color:

commonly near Red Group 52B with a basal spot of near Yellow Group 6B. — petaloid number: commonly 3 on average. — petaloid length: approximately 5.2 cm on average. — petaloid width: approximately 1.0 cm on average. — fragrance: very slight. — petal color when first and fully open: upper surface: commonly near Red Group 52B with a basal spot of commonly near Yellow Group 6B. under surface: commonly near Red Group 52C with a basal spot of commonly near Yellow Group 6C. — petal color at end of blooming: upper surface: commonly near Red Group 53C with a basal spot of near Yellow Group 4D. under surface: commonly near Red Group 53D with a basal spot of near White Group 155B.

*Stamen*.—Number is approximately 122 on average. — anthers: number is approximately 122 on average; coloration is commonly near Greyed-Orange Group 167A; length is approximately 1.0 mm on average; and shape is oval. filaments: length is approximately 7.0 mm on average and coloration is commonly near Yellow Group 9A.

*Pistils*.—Arrangement is separate and free; number is approximately 43 on average. — styles: length is approximately 4.5 mm on average and color is commonly near Green-Yellow Group 1D. stigmas: diameter is typically less than 1.0 mm; coloration is commonly near Green-Yellow Group 1A, and shape is fan shaped.

*Pollen*.—Color is commonly near Greyed-Orange Group 163B and an abundant amount is present.

*Hips*.—None observed.

Development:

*Vegetation*.—Glossy, dark green, vigorous and strong.

*Blooming*.—Abundant and substantially continuous from May to November in Southeastern Pennsylvania.

*Resistance to disease*.—Very good resistance for black spot (*Diplocarpon rosae*) and powdery mildew (*Sphaerotheca pannosa*).

*Hardiness*.—Hardy to USDA Zone 5.

The new 'Sprogreatpink' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Floribunda Rose plant characterized by the following combination of characteristics:

(a) forms attractive, cup-like shaped, deep pink colored blossoms abundantly and substantially continuously, (b) displays a very bushy and compact growth habit, (c) forms vigorous vegetation, and (d) provides attractive ornamental glossy, dark green foliage;

substantially as herein shown and described.

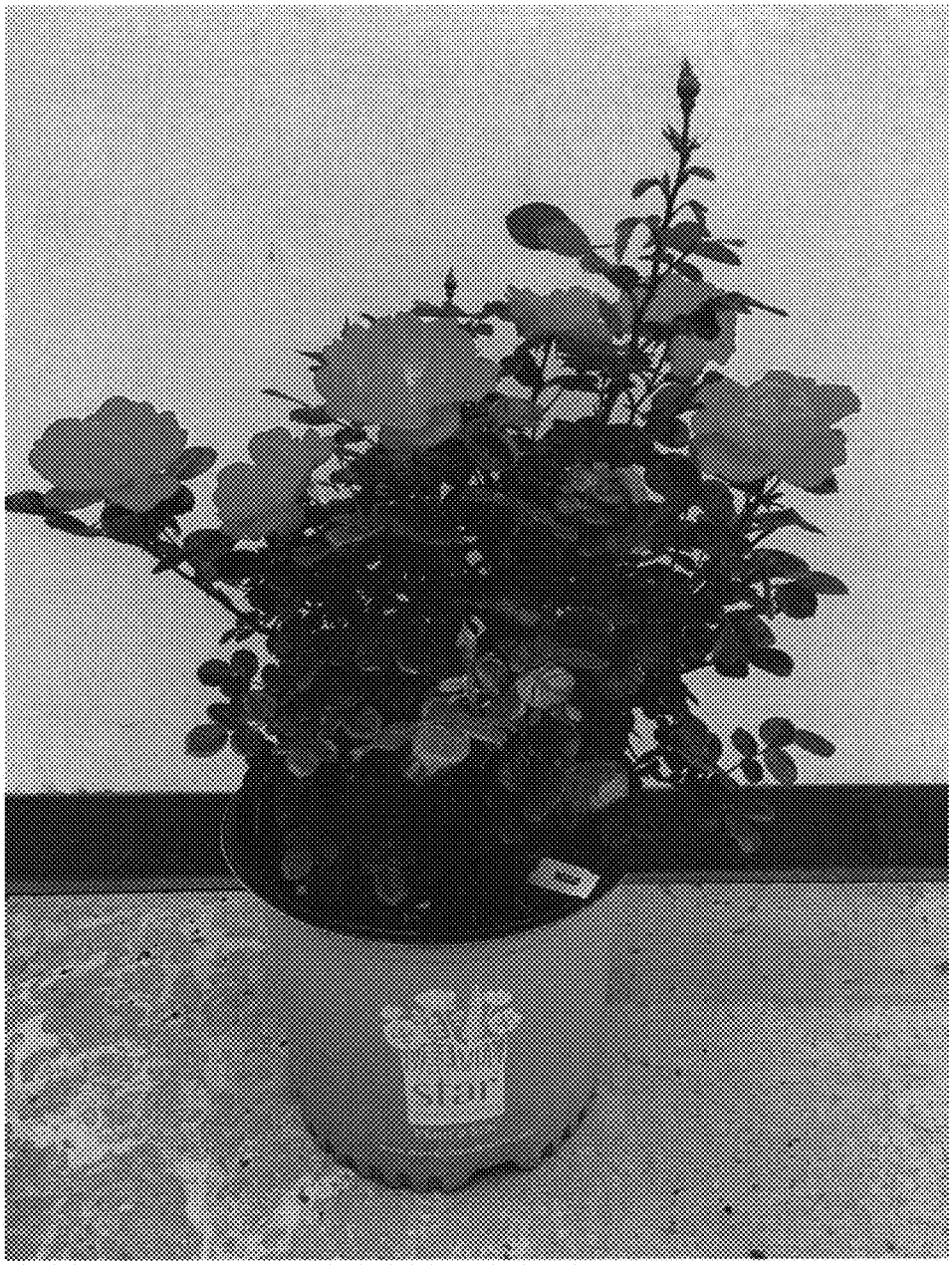

* * * * *